United States Patent [19]

Heeres

[11] 4,154,738

[45] May 15, 1979

[54] IMIDAZOLE DERIVATIVES AND INTERMEDIATES IN THEIR PREPARATION

[75] Inventor: Jan Heeres, Vosselaar, Belgium

[73] Assignee: Janssen Pharmaceutica N.V., Beerse, Belgium

[21] Appl. No.: 917,710

[22] Filed: Jun. 21, 1978

Related U.S. Application Data

[60] Division of Ser. No. 802,700, Jun. 2, 1977, which is a division of Ser. No. 732,827, Oct. 15, 1976, Pat. No. 4,101,665, which is a continuation-in-part of Ser. No. 619,863, Oct. 6, 1975, abandoned, which is a continuation-in-part of Ser. No. 544,157, Jan. 27, 1975, Pat. No. 3,936,470.

[51] Int. Cl.$^2$ .............................. C07D 333/00
[52] U.S. Cl. .................... 260/329 R; 260/329 S; 260/332.2 R; 260/332.3 R; 260/332.5
[58] Field of Search .................... 260/329 R

[56] References Cited

PUBLICATIONS

Chem. Abstracts 79:P152155g.
Chem. Abstracts 83:114255f.
Person et al., Bull. Soc. Chim. Belges, 79, pp. 575–584 (1970).

*Primary Examiner*—Ethel G. Love
*Attorney, Agent, or Firm*—Salvatore R. Conte

[57] ABSTRACT

Novel 1-(2-Ar-4-aryloxymethyl-1,3-dioxolan-2-ylmethyl)-imidazoles, useful as antifungal and antibacterial agents.

1 Claim, No Drawings

IMIDAZOLE DERIVATIVES AND INTERMEDIATES IN THEIR PREPARATION

CROSS-REFERENCE TO RELATED APPLICATIONS

This is a division of application Ser. No. 802,700, filed June 2, 1977 which in turn is a division of Ser. No. 732,827 filed Oct. 15, 1976, now U.S. Pat. No. 4,101,665 which in turn is a continuation-in-part of Ser. No. 619,863, filed Oct. 6, 1975, now abandoned, which in turn is a continuation-in-part of Ser. No. 544,157, filed Jan. 27, 1975 now issued as U.S. Pat. No. 3,936,470.

PRIOR ART

In U.S. Pat. Nos. 3,575,999 and 3,717,655 are described some 1-(2-aryl-1,3-dioxolan-2-ylmethyl)imidazoles. The compounds of this invention differ from the foregoing essentially by the nature of the aryloxymethyl substituent, present in the 4-position of the dioxolane group.

DESCRIPTION OF THE INVENTION

The invention relates to novel imidazole derivatives having the formula:

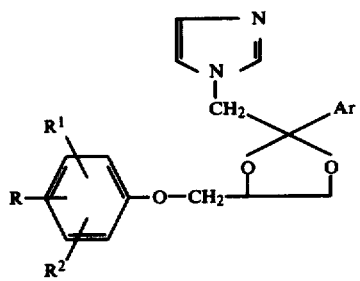

and the therapeutically acceptable acid addition salts thereof, wherein:

Ar is a member selected from the group consisting of phenyl, substituted phenyl, thienyl, halothienyl and naphthyl, and wherein said substituted phenyl is phenyl having from 1 to 3 substituents independently selected from the group consisting of halo, lower alkyl, lower alkyloxy, nitro and cyano.

R is a member selected from the group consisting of nitro, benzoyl, halobenzoyl, lower alkylcarbonyl, lower alkyloxycarbonyl and trifluoromethyl; and $R^1$ and $R^2$ are each independently selected from the group consisting of hydrogen, halo, lower alkyl and lower alkyloxy.

More particularly as used herein "lower alkyl" is meant to include straight and branch chained alkyl radicals having from 1 to about 6 carbon atoms, such as, for example, methyl, ethyl, propyl, 1-methylethyl, 1,1-dimethylethyl, butyl, pentyl, hexyl and the like alkyls; and the term halo is generic to halogens of atomic weight less than 127, i.e., fluoro, chloro, bromo and iodo.

The compounds of formula (I) are conveniently prepared by reacting imidazole (II) with an appropriate reactive ester of formula (III) wherein Ar and R are as previously defined and wherein W is a reactive ester function, such as, for example, halo, 4-methylbenzenesulfonate, methylsulfonate and the like. Preferred reactive esters are halides and more particularly bromides and chlorides.

In one method of conducting the reaction between imidazole and (III), imidazole is first transformed into a metal salt thereof by treatment with an appropriate metallating agent such as, for example, a metal alkoxide, e.g., sodium- or potassium methanolate, or a metal hydride such as sodium hydride. The thus obtained metal salt is then reacted with (III) in an appropriate organic solvent, such as, for example, dimethylformamide or dimethylacetamide. A small amount of a metal iodide, such as sodium or potassium iodide may advantageously be added to promote the reaction, especially when the reactive ester is a chloride or bromide.

Alternatively, the reaction of imidazole with the reactive ester (III) may also be carried out without previous salt formation, by bringing the reactants into contact with each other in an appropriate organic solvent such as, for example, dimethylformamide or dimethylacetamide. In these circumstances it is appropriate to use an excess of imidazole or to add to the reaction mixture an appropriate base such as, for example, sodium or potassium carbonate or bicarbonate in order to bind the acid which is liberated during the course of the reaction. The use of an excess of imidazole is however preferred. Further it is advantageous to conduct the reaction in the presence of a metal iodide such as, for example, sodium or potassium iodide.

In each of the above procedures, somewhat elevated temperatures may be employed to enhance the rate of the reaction and most conveniently the reactions are carried out at the reflux temperature of the reaction mixture.

In these and the following preparations the reaction products may be isolated from the medium and, if necessary, further purified according to methodologies generally known in the art, such as, for example, extraction, trituration, crystallization, chromatography, etc.

The foregoing procedures are more fully illustrated by the following schematic representation:

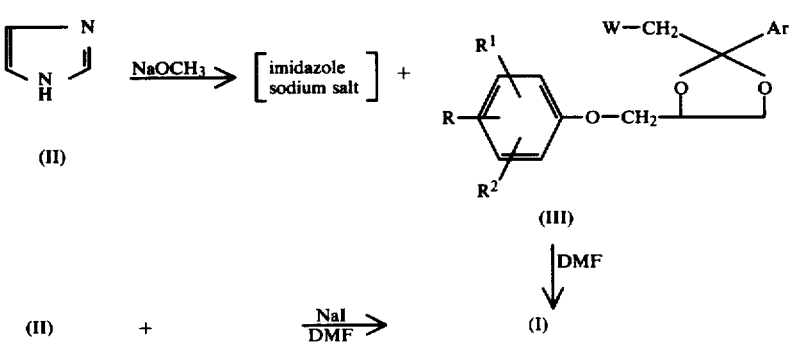

The compounds of formula (I) may still be prepared by the reaction of an appropriate reactive ester of formula (V) wherein Ar and W are as defined hereinbefore with an appropriate phenol of formula (IV), wherein R, R¹ and R² are as previously defined, according to common O-alkylating procedures. Preferably the reaction is carried out in a suitable organic solvent such as, for example, dimethylformamide or dimethylacetamide in the presence of an appropriate metal base such as, for example, sodium hydride, sodium carbonate, potassium carbonate and the like.

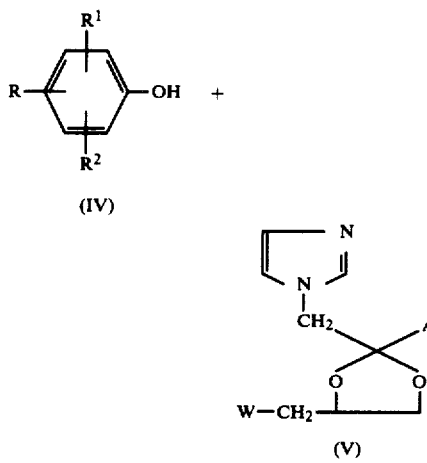

The imidazole derivatives of formula (I), obtained in base form in the foregoing preparations, may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propanoic, hydroxyacetic, α-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic, benzoic, 3-phenylpropenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

The intermediates of formula (III) may be prepared by subjecting an appropriate ketone of formula (VI) wherein Ar and W are as previously defined to a ketalization reaction with an appropriate diol of formula (VII) wherein R, R¹ and R² have the same meaning as assigned to them previously.

Said ketalization reaction may be carried out following methodologies analogous to those described in the literature, e.g., for the preparation of 2-bromomethyl-2,4-diphenyl-1,3-dioxolane [Synthesis, 1974 (I), 23].

In a preferred manner of carrying out the reaction both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as 4-methylbenzenesulfonic acid. Suitable organic solvents are, for example, aromatic hydrocarbons, such as benzene, methylbenzene, dimethylbenzene and the like and saturated hydrocarbons, such as cyclohexane.

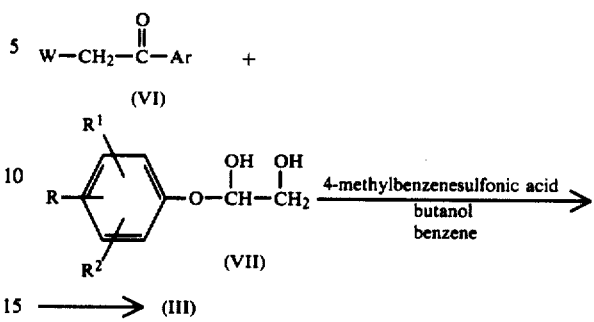

The intermediates of formula (III) are deemed to be novel and as useful intermediates herein they constitute an additional feature of this invention.

A number of the precursor glycols of formula (VII) are known and they may all be prepared according to known procedures as described in the literature. For example, said diols may be prepared by first reacting an appropriate phenol of formula (IV) with an appropriate 2-(halomethyl)oxirane of formula (VIII) following common O-alkylating procedures as generally known in the art, and thereafter subjecting the thus obtained 2-(phenoxymethyl)oxiranes of formula (IX) to hydrolytic cleavage of the oxirane nucleus with an appropriate strong acid such as, for example, ethanedioic acid, sulfuric acid, hydrochloric acid and the like.

The foregoing reactions are illustrated hereafter.

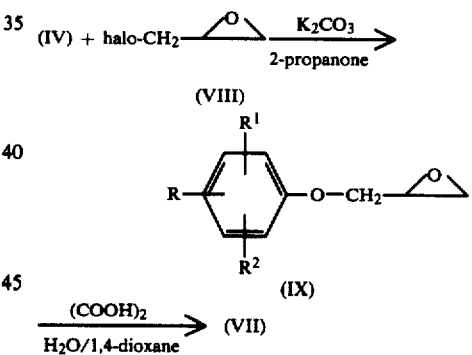

The intermediates of formula (V) may conveniently be prepared by ketalizing an appropriate 1-aroylmethyl-1H-imidazole of formula (X) with an appropriate diol of formula (XI) in a similar manner as described hereinabove for the preparation of (III) starting from (IV) and (V). Otherwise the same intermediates (V) may be obtained by first ketalizing (X) with 1,2,3-propanetriol, and thereafter converting the hydroxyl group of the thus obtained (XII) into a reactive ester group following standard methods of reactive ester formation. For example, methanesulfonates and 4-methylbenzenesulfonates are conveniently prepared by the reaction of the hydroxyl compound with respectively methanesulfonyl chloride or 4-methylbenzenesulfonyl chloride and halides may be prepared by the reaction of the hydroxyl compound with an appropriate halogenating agent such as, for example, sulfuryl chloride, phosphor pentachloride, phosphor pentabromide, phosphoryl chloride and the like. When the reactive ester is an iodide, it is preferably prepared from the corresponding chloride or bromide by the replacement of that halogen with iodine.

The foregoing reactions are illustrated as follows:

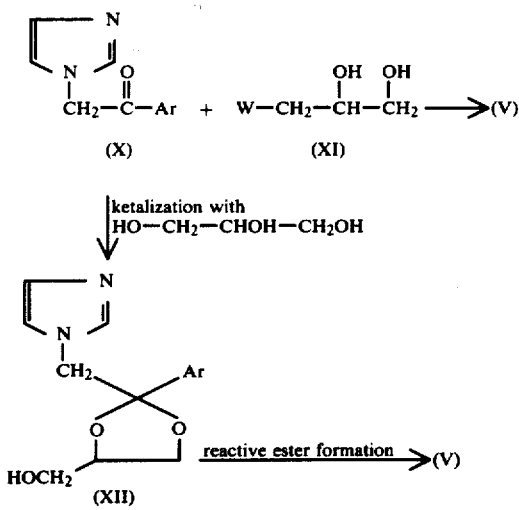

The precursor arylketones of formula (VI) are generally known and may be prepared according to known procedures as described in the literature. Bromides are, for example, easily obtained by the bromination of the corresponding methyl aryl methanone with bromine.

The aroylmethyl substituted imidazoles of formula (X), a number of which are described in U.S. Pat. No. 3,717,655, are conveniently prepared by the reaction of (VI) with imidazole in an analogous manner as previously described for the preparation of the compounds (I) starting from imidazole and (III).

The diastereomeric racemates of (I), denoted as cis and trans forms respectively, according to the rules described in "Naming and Indexing of Chemical Substances for Chemical Abstracts during the 9th Collective Period (1972-1976)", published in C.A. 1972, 76, Index Guide Section IV, p. 85, may be obtained separately by conventional methods. Appropriate methods which may advantageously be employed therefor include, for example, selective crystallization and column-chromatography. For a number of compounds the stereochemical configuration was experimentally determined. In the remaining cases it is conventionally agreed to designate the stereochemical form which is first isolated as "A" and the second as "B" without further reference to the actual stereochemical configuration.

Since the asymmetric carbon atoms are already present in the intermediates (III) and (X) it is also possible to separate cis and trans forms, or generally "A" and "B" forms at this stage, from which the corresponding forms of (I) may be derived. The separation of intermediates of formula (III) and formula (X) may be performed by conventional methods as described hereinbefore for the separation of the compounds (I) into their cis and trans forms.

When an intermediate of formula (X) has to be resolved it may be appropriate to esterify first the hydroxyl group of said (X) with an appropriate acyl halide, e.g., benzoyl chloride whereupon the thus obtained esters are separated into their cis and trans forms, from which the acyl group is subsequently split off hydrolytically in alkaline medium yielding the corresponding form of (X).

It is evident that the cis and trans diastereomeric racemates may be further resolved into their optical isomers, cis(+), cis(−), trans(+) and trans(−) by the application of methodologies known to those skilled in the art.

The compounds of formula (I) and the acid addition salts thereof are useful agents in combatting fungi and bacteria. As such they are valuable in the treatment of human beings, animals and plants suffering from pathogenic microorganisms and in the destruction of microorganisms on materials. The broad spectrum of antifungal and antibacterial activity of the compounds of formula (I) is clearly illustrated by the experimental data presented hereafter. The compounds in the tables are not listed for the purpose of limiting the invention thereto, but only in order to exemplify the useful properties of all the compounds within the scope of formula (I).

The test for antifungal activity was performed using Sabouraud's liquid medium in test tubes each containing 4.5 ml of liquid medium, autoclaved at 120° C. for 15 minutes. The substances were dissolved in 50% ethanol at a concentration of 20 mg/ml and subsequently diluted with sterile distilled water to a concentration of 10 mg/ml. Successive decimal dilutions were then made with distilled water to give a series of stock solutions. To each tube containing 4.5 ml of Sabouraud's liquid medium was added 0.5 ml of one of the stock solutions to give a concentration of the drug under investigation of 100 µg, 10 µg, 1 µg or 0.1 µg per ml of medium. Filamentous fungi were incubated at 25° C. for 2-3 weeks. A square block of side 2 mm. was excised and inoculated into the liquid medium. A three-day old culture on Sabouraud's liquid medium was used for yeasts, and the inoculum was 0.05 ml per tube. All the cultures were incubated at 25° C. for 14 days. The final readings were taken after two weeks and are summarized in the Tables I as follows:

+ + + + = complete inhibition of growth at 0.1 µg/ml
+ + + = complete inhibition of growth at 1 µg/ml
+ + = complete inhibition of growth at 10 µg/ml
+ = complete inhibition of growth at 100 µg/ml
0 = no effect, i.e. growth was observed at the highest concentration tested (100 µg/ml).

In a first screening the drugs under investigation were tested against the following 11 fungi:

1. *Microsporum canis* (M.c. in the tables)
2. *Ctenomyces mentagrophytes* (Ct. m. in the tables)
3. *Trichophyton rubrum* (Tr.r. in the tables)
4. *Phialophora verrucosa* (Ph. v. in the tables)
5. *Cryptococcus neoformans* (Cr. n. in the tables)
6. *Candida tropicalis* (C.tr. in the tables)
7. *Candida albicans* (C. alb. in the tables)
8. *Mucor* species (Muc. in the tables)
9. *Aspergillus fumigatus* (A.f. in the tables)
10. *Sporotrichum schenckii* (Sp. s. in the tables)
11. *Saprolegnia* species (Sap. in the tables)

Bactericidal tests were performed on cultures on phenol red dextrose broth Difco medium. The same decimal dilution techniques as described herebefore were used. The inoculum consisted of a platinum loop (5 mm. diameter) from a 24 hour broth culture.

48 Hours after incubation, subcultures were made from each culture and for the assessment of the bactericidal activity of the drugs under investigation the presence or absence of growth after 7 days incubation was scored as described above.

The substances were tested against the following gram-positive bacilli and cocci:

1. *Erysipelothrix insidiosa* (E. ins. in the table),
2. *Staphylococcus hemolyticus* (Staph. in the table), and
3. *Streptococcus pyogenes* (Strept. in the table).

The results are summarized in Table II.

TABLE I

ANTIFUNGAL ACTIVITY

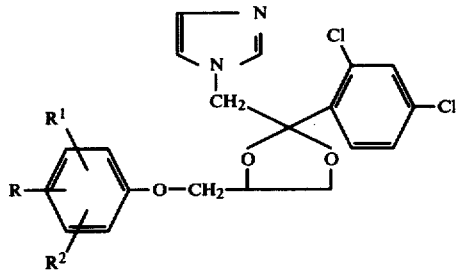

| R,R¹,R² | Isomer | M.c. (1) | Ct.m. (2) | Tr.r. (3) | Ph.v. (4) | Cr.n. (5) | C. tr. (6) | C. alb. (7) | Muc. (8) | A.f. (9) | Sp. s. (10) | Sap. (11) |
|---|---|---|---|---|---|---|---|---|---|---|---|---|
| 4-(C₆H₅—CO) | cis | ++ | +++ | +++ | + | +++ | +++ | 0 | 0 | + | 0 | 0 |
| 2-(C₆H₅—CO)-4-Cl-5-CH₃ | cis | + | ++ | + | 0 | 0 | 0 | 0 | 0 | 0 | + | 0 |
| 4-(CH₃—O—CO) | cis | ++ | +++ | +++ | ++ | +++ | + | 0 | 0 | ++ | +++ | + |
| 2-(C₆H₅—CO)-4-CH₃ | cis | + | +++ | +++ | 0 | + | 0 | 0 | 0 | + | + | + |
| 3-CF₃ | cis | +++ | +++ | +++ | + | +++ | 0 | 0 | + | ++ | ++ | + |
| 4-(CH₃—CO) | cis | +++ | +++ | +++ | ++ | +++ | ++ | 0 | 0 | ++ | ++ | ++ |
| 2-(CH₃—O—CO) | cis | ++ | +++ | +++ | + | +++ | 0 | 0 | + | + | + | + |
| 4-(C₂H₅—CO) | cis | ++ | +++ | +++ | ++ | +++ | 0 | 0 | 0 | ++ | +++ | + |
| 2,6-(OCH₃)₂-4-(CH₃CO) | cis | + | ++ | ++ | 0 | + | 0 | 0 | 0 | 0 | 0 | 0 |
| 2-(CH₃CO)-4-CH₃ | cis | ++ | +++ | +++ | + | +++ | 0 | 0 | 0 | ++ | ++ | + |
| 2-(CH₃CO)-5-OCH₃ | cis | ++ | +++ | +++ | + | ++ | 0 | 0 | 0 | ++ | + | + |
| 2-(C₂H₅CO) | cis | ++ | +++ | +++ | 0 | ++ | 0 | 0 | 0 | + | ++ | + |
| 4-(nC₃H₇OCO) | cis | + | +++ | +++ | + | +++ | + | 0 | 0 | 0 | +++ | + |
| 2-OCH₃-4-(CH₃CO) | cis | ++ | +++ | ++ | + | +++ | + | 0 | 0 | + | + | + |
| 4-(C₂H₅O—CO) | cis | 0 | +++ | 0 | 0 | +++ | 0 | 0 | 0 | 0 | 0 | 0 |
| 2-NO₂-5-Cl | cis | ++ | +++ | +++ | 0 | +++ | 0 | 0 | 0 | 0 | 0 | 0 |
| 2-NO₂ | cis | ++ | +++ | +++ | + | +++ | ++ | 0 | 0 | ++ | ++ | + |
| 2-NO₂ | trans | ++ | +++ | ++ | + | + | 0 | 0 | 0 | ++ | + | 0 |
| 4-(nC₄H₉O—CO) | cis | + | +++ | ++ | + | +++ | +++ | 0 | 0 | 0 | +++ | + |

TABLE II

BACTERIOSTATIC AND BACTERIOCIDAL ACTIVITY

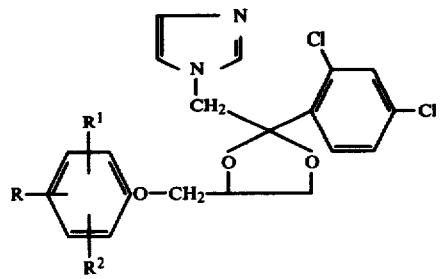

| R, R¹, R² | Isomer | bacteriostatic activity | | | bacteriocidal activity | | |
|---|---|---|---|---|---|---|---|
| | | E. ins. | Staph. | Strept. | E. ins. | Staph. | Strept. |
| 4-(C₆H₅—CO) | cis | +++ | + | +++ | +++ | + | ++ |
| 2-(C₆H₅—CO)-4-Cl-5-CH₃ | cis | +++ | + | +++ | +++ | + | +++ |
| 4-(CH₃—O—CO) | cis | +++ | ++ | +++ | +++ | 0 | + |
| 2-(C₆H₅—CO)-4-CH₃ | cis | +++ | ++ | +++ | +++ | + | ++ |
| 2-(4-Cl—C₆H₄—CO)-5-OCH₃ | cis | 0 | 0 | + | 0 | 0 | + |
| 2-(C₆H₅—CO)-5-OCH₃ | cis | +++ | 0 | ++ | +++ | 0 | ++ |
| 3-CF₃ | cis | +++ | +++ | +++ | +++ | ++ | +++ |
| 4-(CH₃—CO) | cis | +++ | + | +++ | +++ | + | +++ |
| 2-(CH₃—O—CO) | cis | +++ | +++ | ++ | +++ | +++ | + |
| 4-(C₂H₅—CO) | cis | +++ | ++ | +++ | +++ | 0 | ++ |
| 2,6-(OCH₃)₂-4-(CH₃CO) | cis | ++ | 0 | 0 | ++ | 0 | 0 |
| 2-(CH₃—CO)-4-CH₃ | cis | +++ | 0 | 0 | +++ | 0 | 0 |
| 2-(CH₃—CO)-5-OCH₃ | cis | +++ | 0 | 0 | +++ | 0 | 0 |
| 2-(C₂H₅—CO) | cis | +++ | 0 | 0 | +++ | 0 | 0 |

TABLE II-continued
BACTERIOSTATIC AND BACTERIOCIDAL ACTIVITY

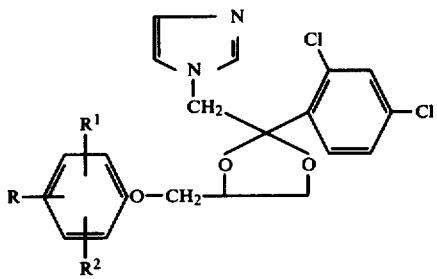

| R, $R^1$, $R^2$ | Isomer | bacteriostatic activity | | | bacteriocidal activity | | |
|---|---|---|---|---|---|---|---|
| | | E. ins. | Staph. | Strept. | E. ins. | Staph. | Strept. |
| 4-($nC_3H_7$—O—CO) | cis | +++ | +++ | +++ | +++ | + | ++ |
| 2-$OCH_3$-4-($CH_3$—CO) | cis | ++ | 0 | ++ | ++ | 0 | ++ |
| 4-($C_2H_5$—O—CO) | cis | +++ | 0 | + | +++ | 0 | 0 |
| 2-$NO_2$-5-Cl | cis | ++ | + | + | ++ | 0 | + |
| 2-$NO_2$ | cis | +++ | ++ | +++ | +++ | + | +++ |
| 2-$NO_2$ | trans | +++ | ++ | +++ | +++ | + | +++ |
| 4-($nC_4H_9$—O—CO) | cis | +++ | ++ | +++ | +++ | + | ++ |

In view of the aforementioned antifungal and antibacterial activities this invention provides valuable compositions comprising the subject 1,3-dioxolan-2-ylmethyl imidazoles (I) or the acid addition salts thereof as the active ingredient in a solvent or a solid, semi-solid or liquid diluent or carrier, and, in addition, it provides an effective method of combatting fungus or bacterial growth by use of an effective anti-fungal or anti-bacterial amount of such ketals (I) or salts thereof. The subject compounds can be used in suitable solvents or diluents, in the form of emulsions, suspensions, dispersions or ointments, on suitable solid or semi-solid carrier substances, in ordinary or synthetic soaps, detergents or dispersion media, if desired, together with other compounds having arachnicidal, insecticidal, ovicidal, fungicidal and/or bactericidal effects, or together with inactive additives.

Solid carrier substances which are suitable for the preparation of compositions in powder form include various inert, porous and pulverous distributing agents of inorganic or organic nature, such as, for example, tricalcium phosphate, calcium carbonate, in the form of prepared chalk or ground limestone, kaolin, bole, bentonite, talcum, kieselguhr and boric acid; powdered cork, sawdust, and other fine pulverous materials of vegetable origin are also suitable carrier substances.

The active ingredient is mixed with these carrier substances, for example, by being ground therewith; alternatively, the inert carrier substance is impregnated with a solution of the active component in a readily volatile solvent and the solvent is thereafter eliminated by heating or by filtering with suction at reduced pressure. By adding wetting and/or dispersing agents, such pulverous preparations can also be made readily wettable with water, so that suspensions are obtained.

Inert solvents used for the production of liquid preparations should preferably not be readily inflammable and should be as far as possible odorless and as far as possible non-toxic to warm-blooded animals or plants in the relevant surroundings. Solvents suitable for this purpose are high-boiling oils, for example, of vegetable origin, and lower-boiling solvents with a flash point of at least 30° C., such as, for example, polyethylen glycols, isopropanol, dimethylsulfoxide, hydrogenated naphthalenes and alkylated naphthalenes. It is, of course, also possible to use mixtures of solvents. Solutions can be prepared in the usual way, if necessary, with assistance of solution promotors. Other liquid forms which can be used consist of emulsions or suspensions of the active compound in water or suitable inert solvents, or also concentrates for preparing such emulsions, which can be directly adjusted to the required concentration. For this purpose, the active ingredient is, for example, mixed with a dispersing or emulsifying agent. The active component can also be dissolved or dispersed in a suitable inert solvent and mixed simultaneously or subsequently with a dispersing or emulsifying agent.

It is also possible to use semi-solid carrier substances of a cream ointment, paste or waxlike nature, into which the active component can be incorporated, if necessary, with the aid of solution promotors and/or emulsifiers. Vaseline and other cream bases are examples of semi-solid carrier substances.

Furthermore, it is possible for the active component to be used in the form of aerosols. For this purpose, the active component is dissolved or dispersed, if necessary, with the aid o suitable inert solvents as carrier liquids, such as difluorodichloro methane, which at atmospheric pressure boils at a temperature lower than room temperature, or in other volatile solvents. In this way, solutions under pressure are obtained which, when sprayed, yield aerosols which are particularly suitable for controlling or combatting fungi and bacteria, e.g., in closed chambers and storage rooms, and for application to vegetation for eradicating or for preventing infections by fungi or bacteria.

The subject compounds and compositions thereof can be applied by conventional methods. For example, a fungus or bacteri growth or a material to be treated or to be protected against attack by fungus or bacterium can be treated with the subject compounds and the compositions thereof by dusting, sprinkling, spraying, brushing, dipping, smearing, impregnating or other suitable means.

When the subject compounds are employed in combination with suitable carriers, e.g., in solution, suspension, dust, powder ointment, emulsion, and the like forms, a high activity over a very high range of dilution is observed. For example, concentrations of the active ingredient ranging from 0.1-10 percent by weight, based on the weight of composition employed, have been found effective in combatting fungi or bacteria. Of course, higher concentrations may also be employed as warranted by the particular situation.

The following examples are intended to illustrate, but not to limit, the scope of the present invention. Unless otherwise stated, all parts are by weight.

EXAMPLE I

A mixture of 10 parts of 1,2,3-propanetriol, 27 parts of 2-bromo-1-(2,4-dichlorophenyl)ethanone, 2 parts of 4-methylbenzenesulfonic acid, 40 parts of 1-butanol and 225 parts of methylbenzene is stirred and refluxed overnight with water-separator. The reaction mixture is cooled, washed with a potassium carbonate solution, dried, filtered and evaporated. The residue is distilled, yielding 21.5 parts (69%) of (A+B)-2-(bromomethyl)-2-(2,4-dichlorophenyl)-1,3-dioxolane-4-methanol; bp. 145°-150° C. at 0.05 mm. pressure.

To a stirred mixture of 67.2 parts of A+B-2-(bromomethyl)-2-(2,4-dichlorophenyl)-1,3-dioxolane-4-methanol and 100 parts of pyridine are added dropwise 27.2 parts of benzoyl chloride while cooling at a temperature below 10° C. Upon completion, stirring is continued for 2.50 hours at room temperature. The reaction mixture is poured onto water and the product is extracted with trichloromethane. The extract is washed successively with a diluted hydrochloric acid solution, to remove the last traces of pyridine, and with water, dried, filtered and evaporated. The oily residue is triturated in methanol. The solid product is filtered off (the filtrate is set aside) and crystallized twice from ethanol, yielding 28 parts of cis-2-(bromomethyl)-2-(2,4-dichlorophenyl)-1,3-dioxolan-4-ylmethyl benzoate; mp. 118.3° C. The filtrate (see above) is evaporated. The oily residue is purified by column-chromatography over silica gel using 2,2'-oxybispropane as eluent. The pure fractions are collected and the eluent is evaporated. The oily residue is triturated in methanol. The solid product is purified by column-chromatography over silica gel using trichloromethane and hexane (30:70) as eluent. The pure fractions are collected and the eluent is evaporated, yielding 17.5 parts of trans-2-(bromomethyl)-2-(2,4-dichlorophenyl)-1,3-dioxolan-4-ylmethyl benzoate; mp. 68.6° C. A mixture of 12 parts of cis-2-(bromomethyl)-2-(2,4-dichlorophenyl)-1,3-dioxolan-4-ylmethyl benzoate, 7.5 parts of a sodium hydroxide solution 60%, 100 parts of water and 200 parts of 1,4-dioxane is stirred and refluxed for one hour. The reaction mixture is allowed to cool to room temperature, poured onto water and the product is extracted with trichloromethane. The extract is washed with water, dried, filtered and evaporated. The residue is purified by column-chromatography over silica gel using a mixture of trichloromethane, hexane and methanol (50:49:1) as eluent. The pure fractions are collected and the eluent is evaporated, yielding 4.5 parts of cis-2-(bromomethyl)-2-(2,4-dichlorophenyl)-1,3-dioxolane-4-methanol as an oily residue.

A mixture of 7.7 parts of 1H-imidazole, 8 parts of cis-2-(bromomethyl)-2-(2,4-dichlorophenyl)-1,3-dioxolane-4-methanol, 1 part of potassium iodide and 180 parts of N,N-dimethylacetamide is stirred and refluxed for 3 days. The reaction mixture is cooled and evaporated. Then there are added 50 parts of water and 300 parts of trichloromethane to the residue. The whole is washed three times with water, dried, filtered and evaporated. The residue is purified by column-chromatography over silica gel using a mixture of trichloromethane and 2% of methanol as eluent. The pure fractions are collected and the eluent is evaporated, yielding 9.2 parts of cis-2-(2,4-dichlorophenyl)-2-(1H-imidazol-1-ylmethyl)-1,3-dioxolane-4-methanol; mp. 140° C.

A mixture of 4.5 parts of methanesulfonyl chloride, 10 parts of cis-2-(2,4-dichlorophenyl)-2-(1H-imidazol-1-ylmethyl)-1,3-dioxolane-4-methanol and 50 parts of pyridine is allowed to stand for 3 hours at room temperature. The reaction mixture is poured onto water. The precipitated product is filtered off and crystallized from benzene, yielding 10.3 parts (87%) of cis-2-(2,4-dichlorophenyl)-2-(1H-imidazol-1-ylmethyl)-1,3-dioxolan-4-ylmethyl methanesulfonate; mp. 111.7° C.

EXAMPLE II

To a stirred solution of 139 parts of 2-nitrophenol and 138 parts of potassium carbonate in 640 parts of 2-propanone are added dropwise 215 parts of 2-(chloromethyl)oxirane. Upon completion, stirring is continued for 2 days at reflux. The formed precipitate is filtered off and the filter-cake is washed with 2-propanone. The filtrate is evaporated. The residue is crystallized from a mixture of 2,2'-oxybispropane and petroleumether (1:1 by volume). The product is filtered off and dried, yielding 38 parts (20%) of 2-(2-nitrophenoxymethyl)oxirane; mp. 56° C.

To a stirred solution of 38 parts of 2-(2-nitrophenoxymethyl)oxirane in 10 parts of ethanedioic acid and 300 parts of 1,4-dioxane are added 100 parts of water. The whole is stirred and refluxed for 2 days. The reaction mixture is evaporated and the residue is crystallized from a mixture of 2,2'-oxybispropane and petroleumether. The product is filtered off and recrystallized from 2,2'-oxybispropane, yielding 29.5 parts (13%) of 3-(2-nitrophenoxy)-1,2-propanediol; mp. 96° C.

A mixture of 14.9 parts of 3-(2-nitrophenoxy)-1,2-propanediol, 13.4 parts of 2-bromo-1-(2,4-dichlorophenyl)ethanone, 3 parts of 4-methylbenzenesulfonic acid, 40 parts of butanol and 225 parts of methylbenzene is stirred and refluxed over week-end. The reaction mixture is evaporated and the oily residue is dissolved in trichloromethane. The solution is washed with a diluted sodium hydroxide solution 20% and with water, dried, filtered and evaporated. The oily residue is crystallized from 2,2'-oxybispropane while stirring. The product is filtered off (the filtrate is set aside), yielding 8.5 parts of A-2-(bromomethyl)-2-(2,4-dichlorophenyl)-4-(2-nitrophenoxymethyl)-1,3-dioxolane. The filtrate which was set aside, is evaporated. The oily residue is purified twice by column-chromatography over silica gel using, first trichloromethane and second a mixture of trichloromethane and 20% of hexane as eluent. The pure fractions are collected and the eluent is evaporated, yielding 14.5 parts of B-2-(bromomethyl)-2-(2,4-dichlorophenyl)-4-(2-nitrophenoxymethyl)-1,3-dioxolane as an oily residue.

EXAMPLE III

A mixture of 13.6 parts of butyl 4-(2,3-dihydroxypropoxy)benzoate, 15.2 parts of 2-bromo-1-(2,4-dichlorophenyl)ethanone, 3 parts of 4-methylbenzenesulfonic acid, 40 parts of 1-butanol and 225 parts of dimethylbenzene is stirred and refluxed for 3 days with water-separator. The reaction mixture is evaporated and the residue is triturated in methanol. The product is filtered off and crystallized from 2-propanol, yielding 8.7 parts (39%) of (A)-butyl 4-[2-(bromomethyl)-2(2,4-dichlorophenyl)-1,3-dioxolan-4-ylmethoxy]benzoate.

EXAMPLE IV

A mixture of 2.2 parts of (4-hydroxyphenyl)phenylmethanone, 4.2 parts of cis-2-(2,4-dichlorophenyl)-2-(1H-imidazol-1-ylmethyl)-1,3-dioxolan-4-ylmethyl methanesulfonate, 2 parts of potassium carbonate and 68 parts of N,N-dimethylformamide is stirred overnight at a temperature of 100° C. The reaction mixture is cooled and poured onto water. The product is extracted twice with 1,1'-oxybisethane. The combined extracts are washed with water, dried, filtered and evaporated. The residue is converted into the nitrate salt in 4-methyl-2-pentanone and 2,2'-oxybispropane, yielding 4.5 parts (78%) of cis-{4-[2-(2,4-dichlorophenyl)-2-(1H-imidazol-1-ylmethyl)-1,3-dioxolan-4-ylmethoxy]phenyl}phenylmethanone nitrate; mp. 179° C.

EXAMPLE V

Following the procedure of Example IV and using an equivalent amount of an appropriate phenol in place of the (4-hydroxyphenyl)phenylmethanone used therein, the following imidazoles and imidazole acid addition salts are prepared:

| $R,R^1,R^2$ | base or acid salt | melting point |
|---|---|---|
| 2-($C_6H_5$—CO),4-Cl, 5-$CH_3$ | $(COOH)_2$ | 170.8° C. |
| 4-($CH_3$—O—CO) | $HNO_3$ | 167.8° C. |
| 2-($C_6H_5$—CO), 4-$CH_3$ | $HNO_3$ | 145.4° C. |
| 2-(4-Cl—$C_6H_4$—CO), 5-$OCH_3$ | base | 168.3° C. |
| 2-($C_6H_5$—CO), 5-$OCH_3$ | base | 149.2° C. |
| 3-$CF_3$ | $HNO_3$ | 152.6° C. |
| 4-($CH_3$—CO) | $HNO_3$ | 182.6° C. |
| 2-($CH_3O$—CO) | $HNO_3$ | 140.5° C. |
| 4-($CH_3$—$CH_2$—CO) | $HNO_3$ | 176.2° C. |
| 2,6-$(OCH_3)_2$,4-($CH_3CO$) | $HNO_3$ | 163.7° C. |
| 2-($CH_3$—CO), 4-$CH_3$ | $HNO_3$ | 158.6° C. |
| 2-($CH_3$—CO), 5-($OCH_3$) | $HNO_3$ | 178.7° C. |
| 2-($CH_3$—$CH_2$—CO) | $HNO_3$ | 193.1° C. |
| 4-($CH_3$—$CH_2$—$CH_2$—O—CO) | $HNO_3$ | 80.4° C. |
| 2-($OCH_3$), 4-($CH_3CO$) | $HNO_3$ | 168.0° C. |
| 4-($CH_3$—$CH_2$—O—CO) | base | 154.6° C. |
| 2-$NO_2$, 5-Cl | base | 101.8° C. |

EXAMPLE VI

A mixture of 6.3 parts of 1H-imidazole, 8.5 parts of A-2-(bromomethyl)-2-(2,4-dichlorophenyl)-4-(2-nitrophenoxymethyl)-1,3-dioxolane, 3 parts of potassium iodide and 180 parts of N,N-dimethylacetamide is stirred and refluxed for 3 days. The reaction mixture is poured onto water and the product is extracted three times with 1,1'-oxybisethane. The combined extracts are washed with water, dried, filtered and evaporated. The residue is coverted into the ethanedioate salt in 4-methyl-2-pentanone and 2,2'-oxybispropane. The salt is filtered off and crystallized from 4-methyl-2-pentanone. The product is filtered off and dried in vacuo, yielding 2.5 parts (25%) of cis-1-[2-(2,4-dichlorophenyl)-4-(2-nitrophenoxymethyl)-1,3-dioxolan-2-yl-methyl]-1H-imidazole diethanedioate; mp. 95.2° C.

EXAMPLE VII

Following the procedure of Example VI there is prepared trans-1-[2-(2,4-dichlorophenyl)-4-(2-nitrophenoxymethyl)-1,3-dioxolan-2-ylmethyl]-1H-imidazole ethanedioate; mp. 157.2° C. by the reaction of imidazole with (B)-2-(bromomethyl)-2-(2,4-dichlorophenyl)-4-(2-nitrophenoxymethyl)-1,3-dioxolane.

EXAMPLE VIII

A mixture of 5.7 parts of 1H-imidazole, 8.7 parts of (A)-butyl 4-[2-(bromomethyl)-2-(2,4-dichlorophenyl)-1,3-dioxolan-4-ylmethoxy]benzoate and 135 parts of N,N-dimethylacetamide is stirred and refluxed for 3 days. The reaction mixture is cooled and poured onto water. The product is extracted twice with 1,1'-oxybisethane. The combined extracts are washed with water, dried, filtered and evaporated. The residue is converted into the nitrate salt in 4-methyl-2-pentanone and 2,2'-oxybispropane. The salt is filtered off and crystallized from a mixture of acetonitrile and 2,2'-oxybispropane. It is filtered off again and dried, yielding 4.9 parts (51%) of cis-butyl 4-[2-(2,4-dichlorophenyl)-2-(1H-imidazol-1-ylmethyl)-1,3-dioxolan-4-ylmethoxy]benzoate nitrate; mp. 90.5° C.

EXAMPLE IX

Following the procedure of Example I and using equivalent amounts of the appropriate starting materials there are prepared:

cis-2-(4-chlorophenyl)-2-(1H-imidazol-1-ylmethyl)-1,3-dioxolan-4-ylmethyl methanesulfonate;

cis-2-(1H-imidazol-1-ylmethyl)-2-(4-methylphenyl)-1,3-dioxolan-4-ylmethyl methanesulfonate;

cis-2-(1H-imidazol-1-ylmethyl)-2-(4-methoxyphenyl)-1,3-dioxolan-4-ylmethyl methanesulfonate;

cis-2-(1H-imidazol-1-ylmethyl)-2-(4-nitrophenyl)-1,3-dioxolan-4-ylmethyl methanesulfonate;

cis-2-(4-cyanophenyl)-2-(1H-imidazol-1-ylmethyl)-1,3-dioxolan-4-ylmethyl methanesulfonate;

cis-2-(1H-imidazol-1-ylmethyl)-2-(2-thienyl)-1,3-dioxolan-4-ylmethyl methanesulfonate;

cis-2-(5-chloro-2-thienyl)-2-(1H-imidazol-1-ylmethyl)-1,3-dioxolan-4-ylmethyl methanesulfonate; and cis-2-(1H-imidazol-1-ylmethyl)-2-(2-naphthalenyl)-1,3-dioxolan-4-ylmethyl methanesulfonate.

EXAMPLE X

Following the procedure of Example IV and using equivalent amounts of the appropriate starting materials there are prepared:

cis-{4-[2-(4-chlorophenyl)-2-(1H-imidazol-1-ylmethyl)-1,3-dioxolan-4-ylmethoxy]phenyl}phenylmethanone;

cis-{4-[2-(1H-imidazol-1-ylmethyl)-2-(4-methylphenyl)-1,3-dioxolan-4-ylmethoxy]phenyl}phenylmethanone;

cis-{4-[2-(1H-imidazol-1-ylmethyl)-2-(4-methoxyphenyl)-1,3-dioxolan-4-ylmethoxy]phenyl}phenylmethanone;

cis-{4-[2-(1H-imidazol-1-ylmethyl)-2-(4-nitrophenyl)-1,3-dioxolan-4-ylmethoxy]phenyl}phenylmethanone;

cis-4-[4-(4-benzoylphenoxymethyl)-2-(1H-imidazol-1-ylmethyl)-1,3-dioxolan-2-yl]benzonitrile;

cis-{4-[2-(1H-imidazol-1-ylmethyl)-2-(2-thienyl)-1,3-dioxolan-4-ylmethoxy]phenyl}phenylmethanone;

cis-{4-[2-(5-chloro-2-thienyl)-2-(1H-imidazol-1-ylmethyl)-1,3-dioxolan-4-ylmethoxy]phenyl}phenylmethanone;

cis-{4-[2-(2-naphthalenyl)-2-(1H-imidazol-1-ylmethyl)-1,3-dioxolan-4-ylmethoxy]phenyl}phenylmethanone;

cis-{5-chloro-2-[2-(4-chlorophenyl)-2-(1H-imidazol-1-ylmethyl)-1,3-dioxolan-4-ylmethoxy]-4-methylphenyl}phenylmethanone;

cis-methyl 4-[2-(1H-imidazol-1-ylmethyl)-2-(4-methylphenyl)-1,3-dioxolan-4-ylmethoxy]benzoate;

cis-{2-[2-(1H-imidazol-1-ylmethyl)-2-(4-methoxyphenyl)-1,3-dioxolan-4-ylmethoxy]-5-methylphenyl}phenylmethanone;

cis-4-{4-[2-(4-chlorobenzoyl)-5-methoxyphenoxymethyl]-2-(1H-imidazol-1-ylmethyl)-1,3-dioxolan-2-yl}benzonitrile;

cis-1-{2-(4-chlorophenyl)-4-[3-(trifluoromethyl)phenoxymethyl]-1,3-dioxolan-2-ylmethyl}-1H-imidazole; and cis-1-{4-[2-(4-chlorophenyl)-2-(1H-imidazol-1-ylmethyl)-1,3-dioxolan-4-ylmethoxy]phenyl}ethanone.

I claim:
1. A chemical compound having the formula

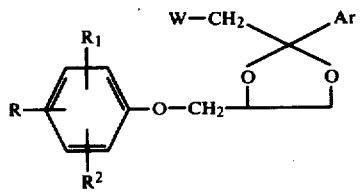

wherein:
W is a member selected from the group consisting of halo, 4-methylphenylsulfonyloxy and methylsulfonyloxy;
Ar is a member selected from the group consisting of thienyl and halothienyl;
R is a member selected from the group consisting of nitro, benzoyl, halobenzoyl, lower alkylcarbonyl, lower alkyloxycarbonyl and trifluoromethyl; and
$R^1$ and $R^2$ are each independently selected from the group consisting of hydrogen, halo, lower alkyl and lower alkyloxy.

* * * * *